United States Patent [19]

Remiszewski et al.

[11] Patent Number: 5,337,937
[45] Date of Patent: Aug. 16, 1994

[54] SURGICAL STAPLING APPARATUS

[75] Inventors: Stanley H. Remiszewski, Greenwich; David T. Green, Westport, both of Conn.

[73] Assignee: United States Surgical Corporation, Norwalk, Conn.

[21] Appl. No.: 52,223

[22] Filed: Apr. 22, 1993

Related U.S. Application Data

[63] Continuation of Ser. No. 781,696, Oct. 18, 1991, abandoned.

[51] Int. Cl.⁵ .......................... A61B 17/068
[52] U.S. Cl. .................. 227/182; 227/176; 227/19
[58] Field of Search ............ 227/19, 175, 176, 177, 227/182, 121

[56] References Cited

U.S. PATENT DOCUMENTS

| | | | |
|---|---|---|---|
| 1,452,373 | 10/1921 | Gomez | 227/19 |
| 2,301,622 | 11/1942 | Hambrecht | 227/177 |
| 2,853,074 | 9/1958 | Olson . | |
| 2,874,384 | 2/1959 | Krone | 227/19 |
| 3,269,631 | 8/1966 | Takaro | 227/19 X |
| 3,278,107 | 10/1966 | Rygg . | |
| 3,604,561 | 9/1971 | Mallina et al. . | |
| 3,638,847 | 2/1972 | Noiles et al. | 227/19 X |
| 3,650,453 | 3/1972 | Smith, Jr. | 227/19 X |
| 4,127,227 | 11/1978 | Green | 227/19 X |
| 4,185,762 | 1/1980 | Froelich . | |
| 4,204,623 | 5/1980 | Green . | |
| 4,471,780 | 9/1984 | Menges | 227/19 X |
| 4,591,086 | 5/1986 | Campbell et al. . | |
| 4,687,098 | 8/1987 | Ebihara . | |
| 4,809,695 | 3/1989 | Gwathmey et al. | 227/19 X |
| 4,821,939 | 4/1989 | Green | 227/19 |
| 4,944,443 | 7/1990 | Oddsen et al. . | |
| 4,991,763 | 2/1991 | Storace . | |

FOREIGN PATENT DOCUMENTS

| | | | |
|---|---|---|---|
| 0167217 | 1/1986 | European Pat. Off. . | |
| 376223 | 5/1964 | Switzerland . | |
| 488448 | 5/1970 | Switzerland . | |
| 1090375 | 5/1984 | U.S.S.R. | 227/175 |
| 1228830 | 5/1986 | U.S.S.R. | 227/175 |
| 1237180 | 6/1986 | U.S.S.R. | 227/175 |
| 319886 | 10/1929 | United Kingdom . | |

*Primary Examiner*—Rinaldi I. Rada

[57] ABSTRACT

A surgical stapling apparatus comprising an anvil jaw pivotally connected to a first handle for movement from an open position to a closed position to clamp body tissue, staple advancing means for advancing an individual staple into contact with the anvil jaw for deformation of the staple legs and means for closing the anvil and for actuating the staple advancing means in a three phase movement of the handles. In the first movement of the handle the anvil jaw pivots to a closed position; in a second subsequent movement of the handles the anvil jaw remains stationary and the staple advancing means is not yet actuated; and in a third movement of the handle the staple advancing means is actuated. This second movement constitutes a dwell period of the apparatus.

35 Claims, 8 Drawing Sheets

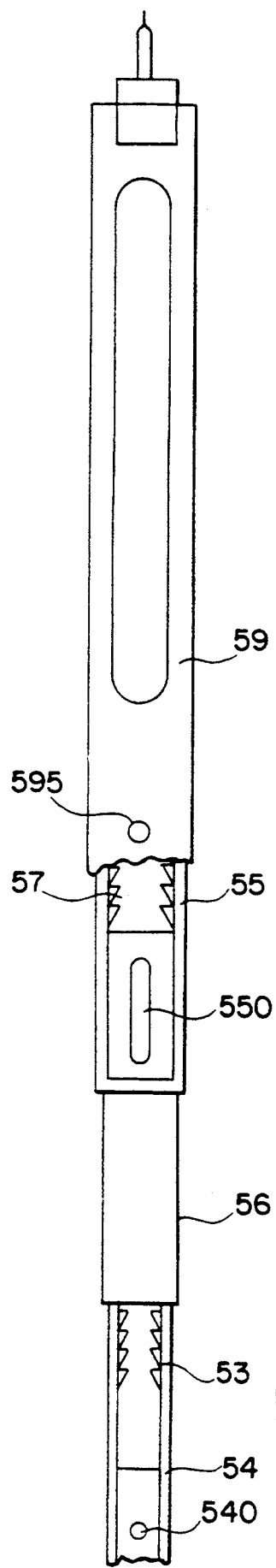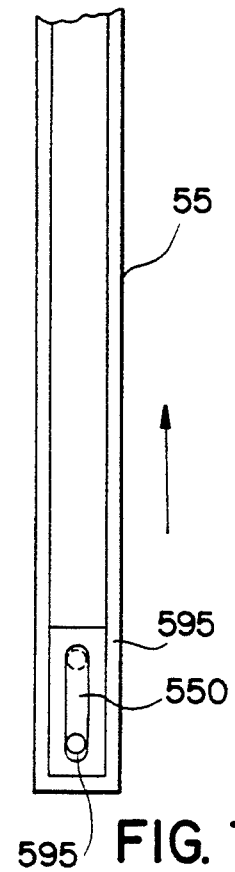
FIG. 7A
FIG. 7B

SURGICAL STAPLING APPARATUS

This is a continuation of copending application Ser. No. 07/781,696 filed on Oct. 18, 1991, now abandoned.

BACKGROUND OF THE INVENTION

1. Field of the Invention

This invention relates to a surgical stapling apparatus, and more particularly to an apparatus for clamping vascular tissue and subsequently driving an individual staple through the tissue and into contact with a staple forming anvil.

2. Description of the Related Art

Surgical apparatus for applying clips to vascular tissue are well known in the art. In these devices, each leg of the clip, typically U-shaped in configuration, is held in one of the opposing jaws of the instrument and the jaws are placed on opposing sides of the vessel. The jaws are then closed to flatten the clip to squeeze the vessel walls together to effect hemostasis. These prior apparatus suffer from the disadvantage that the clip can only be advanced into the jaws of the instrument when the jaws are open so that vessel clamping and clip closing occur simultaneously. As a result, the surgeon cannot first ensure the vessel is properly clamped before committing to clip closure. Another disadvantage of these clip appliers is they can only be utilized to close a single vessel since they straddle the vessel; they cannot be used to attach approximated vessels or vessel portions.

Another prior method for repairing vascular tissue is suturing. Although two approximated vessels can be attached by this method, it is not only time consuming, but is difficult to accomplish in certain procedures, especially when the vessel is not in an easily accessible location or when microvascular tissue is involved. Still another disadvantage of suturing is that numerous punctures are made in the vessel walls since a hole is created with each passage of the suture needle.

Instruments for applying single staples one at a time to body tissue are also known. These instruments differ from the clip appliers in that they provide one jaw which contains a staple and an opposing jaw which contains an anvil for deforming the legs of the staple. For example, U.S. Pat. No. 3,278,107 discloses a device where closing of the handles clamps the vessels and forms a single staple. This instrument suffers from the disadvantage associated with the above described clip appliers since clamping of the tissue and application of the staple occur simultaneously. U.S. Pat. No. 3,604,561 also discloses a stapler having a pair of clamping jaws and a mechanism for advancing the staple into an anvil. When sufficient force is applied to the handles, the staple is driven through the tissue and into the anvil. This instrument is deficient in that premature firing could occur if too much force is applied to the handles during the initial clamping action. Additionally, the surgeon cannot readily differentiate when the tissue clamping is completed and the staple firing stroke is initiated within sufficient time to unclamp the tissue.

The need therefore exists for an improved surgical stapler which can apply staples one at a time to body tissue such as vascular tissue and in which the user can unclamp the tissue engaging jaws before firing a staple. The need also exists for an instrument which could indicate to the user when the tissue clamping action is complete and the staple firing mechanism is about to be actuated. Such an instrument could be utilized for closing individual vessels as well as attaching approximated vessels.

SUMMARY OF THE INVENTION

The present invention overcomes the disadvantages and deficiencies of prior apparatus by providing a surgical stapling apparatus comprising an anvil jaw pivotally connected to a first handle for movement from an open position to a closed position to clamp body tissue, staple advancing means for advancing an individual staple into contact with the anvil jaw for deformation of the staple legs, and means for closing the anvil and for actuating the staple advancing means in a three phase movement of the handles. In the first movement of the handles the anvil jaw pivots to a closed position; in a third movement of the handle the staple advancing means is actuated; and in a second movement which occurs between the first and third movements, the anvil jaw remains stationary and the staple advancing means is not yet actuated. This second movement constitutes a dwell period of the apparatus.

A link member may be provided to connect the first handle to the anvil jaw wherein the link member has an angled camming slot cooperating with a pin connected to the first handle. The camming slot has a diagonal or angled portion and a vertical portion The pin first travels in the angled portion to advance the first link member to pivot the anvil jaw to a closed position, and during subsequent travel of the pin in the vertical position the link remains stationary. A second link member connecting the first handle to the staple advancing means may be provided wherein the second link member includes an angled camming slot cooperating with a pin connected to the first handle. The camming slot has a vertical portion and an angled portion so that when the pin first travels in the vertical portion the link member remains stationary, and when the pin subsequently travels in the angled portion the link member is moved so the staple advancing means is actuated. At least a portion of the vertical portions of the camming slots overlap. Travel of the pin in this overlapping portion occurs upon the second movement of the handle, during the dwell period.

In another aspect of the present invention, a staple cartridge is provided comprising a first rack having a plurality of teeth, a stack of staples longitudinally aligned in the rack, and means for advancing the staple stack distally. The staple stack advancing means comprises a stack pusher positioned in abutment with a proximalmost staple and engaging the teeth of the first rack. Means for advancing the stack pusher distally over the teeth includes means for preventing proximal movement of the stack pusher.

In a preferred embodiment, the stack pusher advancing means comprises a second rack positioned over the first rack and the preventing means comprises a plurality of teeth formed in the second rack and engaging the staple pusher. The first rack preferably remains stationary during advancement of the second rack. Movement of the second rack is initiated only after individual staple advancing means has advanced a predetermined distance.

BRIEF DESCRIPTION OF THE DRAWINGS

The foregoing objects and other features of the present invention will become more readily apparent and may be understood by referring to the following detailed description of an illustrative embodiment of the surgical stapling instrument taken in conjunction with the accompanying drawings in which:

FIG. 7A is an enlarged top view of the staple cartridge;

FIG. 7B is an enlarged top view of the upper rack of the staple cartridge;

DETAILED DESCRIPTION OF THE PREFERRED EMBODIMENT

Figure 1:
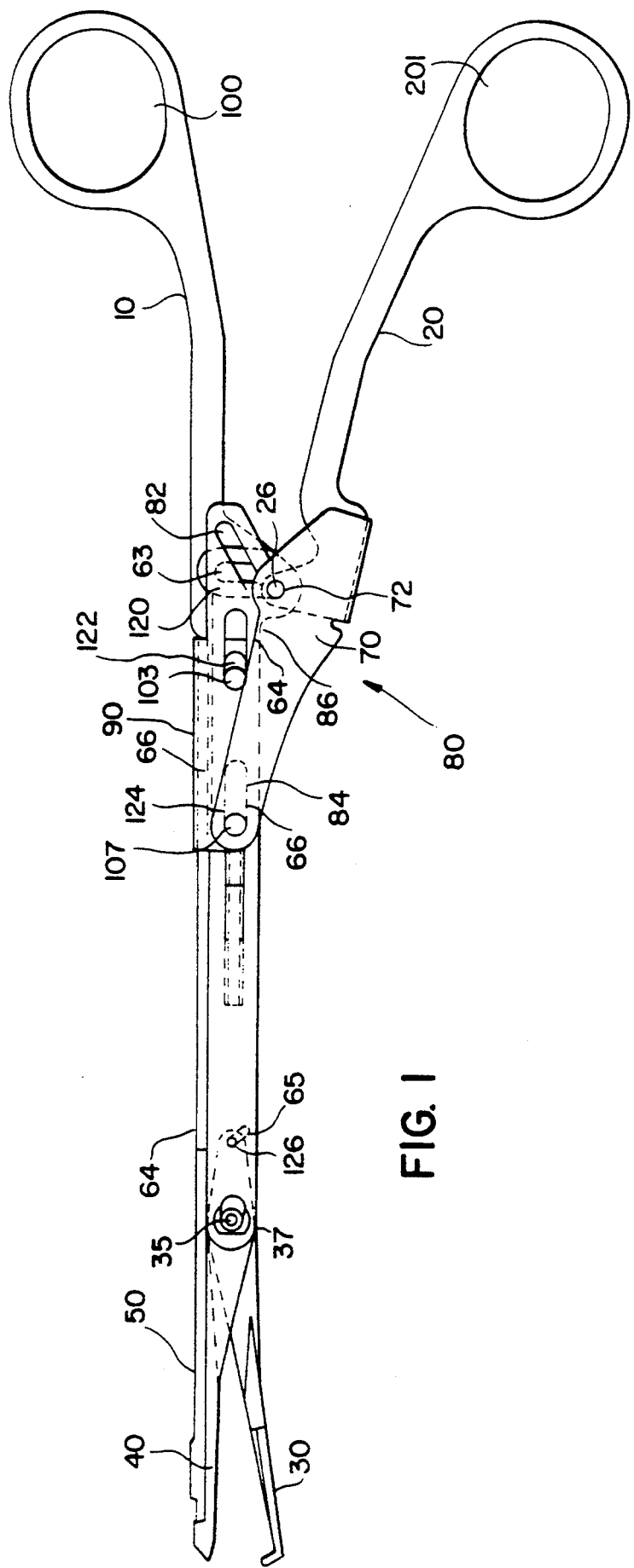
FIG. 1 illustrates a side view showing the apparatus of the present invention in the open position.
Figure 3:
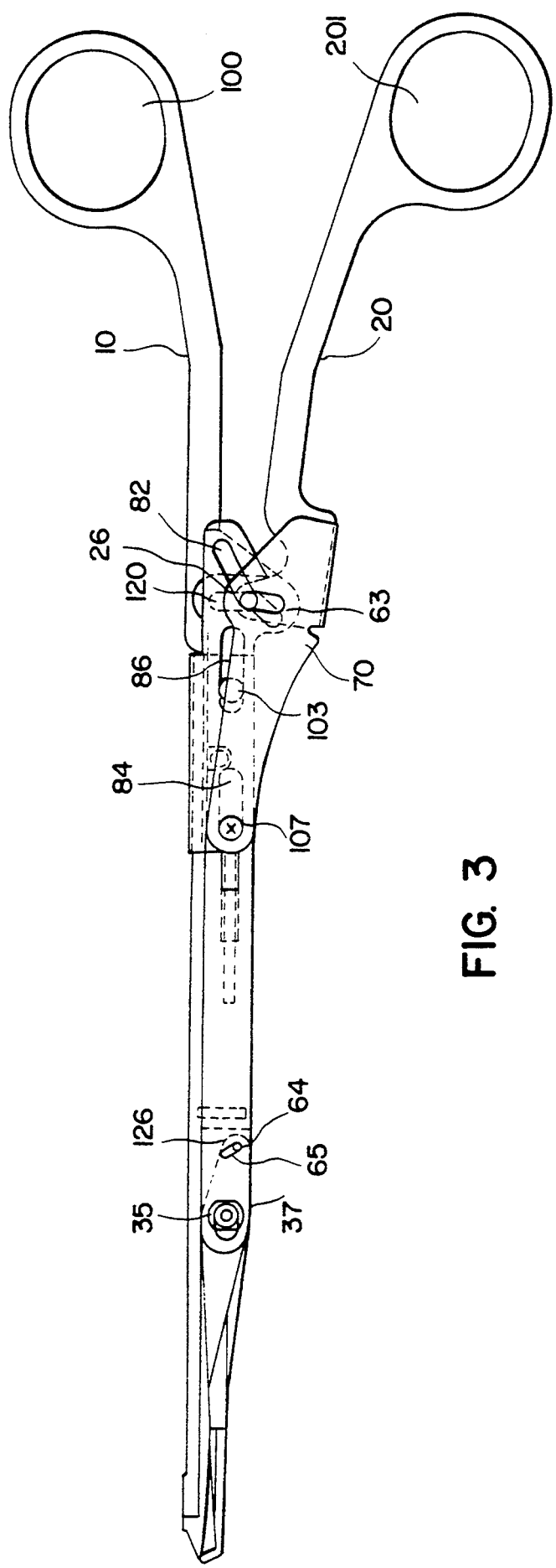
FIG. 3 is a side view of the apparatus in the clamped, unfired position.

Referring now to the drawings in which like reference numerals represent identical or similar parts throughout the several views, FIG. 1 illustrates the surgical apparatus of the present invention for driving staples one at a time through body tissue and against a staple deforming anvil. The apparatus comprises an actuating handle 20, an anvil jaw 30 coupled to the actuating handle 20, and a stationary elongated handle 10 terminating at its distal end in a staple carrying jaw 40. Anvil jaw 30 is positioned opposite staple carrying jaw 40 and is pivotable around pin 107 by handle 20 from an open position spaced from staple carrying jaw 40 (FIG. 1) to a closed position adjacent staple carrying jaw 40 to clamp tissue therebetween (FIG. 3). A staple cartridge 50 is mounted atop staple carrying jaw 40 and includes a pusher member for driving the individual staples which is also actuated by handle 20. Both handles 10 and 20 terminate at their proximal ends in finger loops 100, 201, respectively, to facilitate manipulation by the user.

Figure 6A:
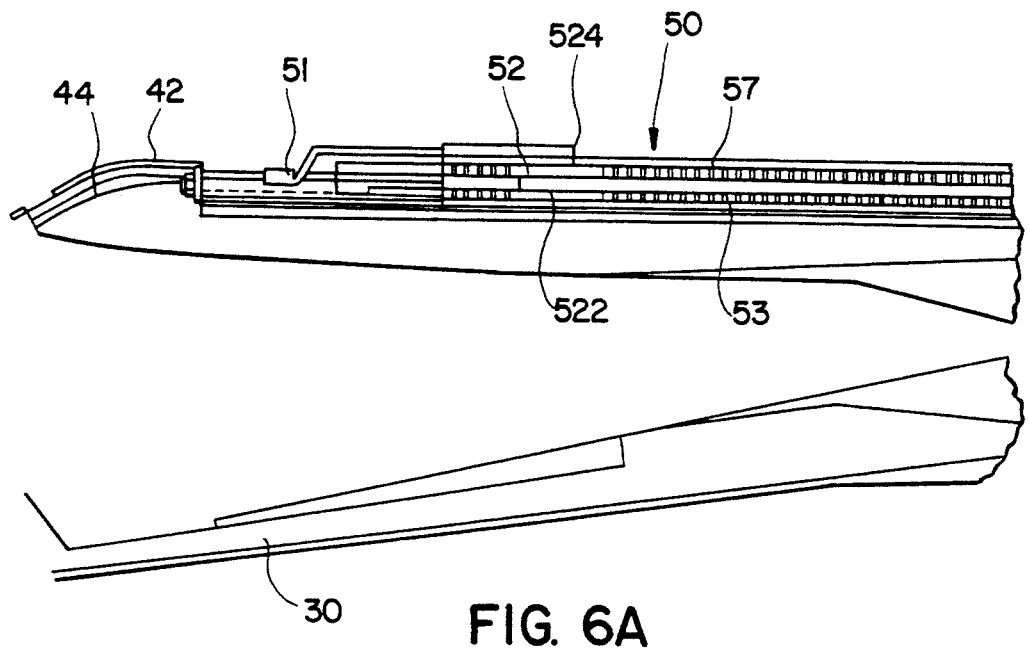
FIG. 6A is an enlarged side view of the distal end of the staple cartridge and anvil jaw in the open position.
Figure 6B:
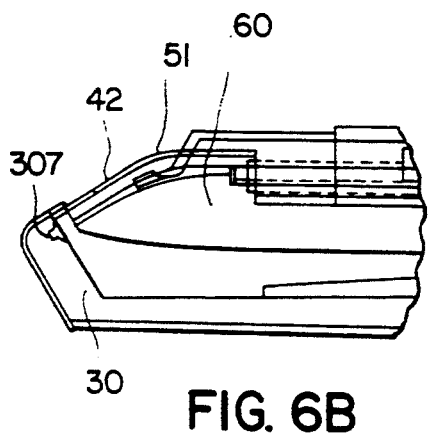
FIG. 6B is an enlarged side view of the distal end of the staple jaw and anvil jaw in the clamped position showing initial advancement of the staple.

Anvil jaw 30 includes a pair of depressions 307 (only one of which is shown in FIGS. 6A, 6B) dimensioned to receive the legs of the staples S to form them into a B-shaped configuration as shown. Anvil jaw 30 preferably includes an angled wall 305 to block the entry of tissue from the instrument as well as to provide a guide for the staples. Wall 305 may optionally terminate in a pair of tissue prongs to further prevent tissue from interfering with the staple pusher or staples during formation.

Referring back to FIG. 1, transverse guide pin 26 forms part of the linkage mechanism for clamping the tissue and driving the staples. Pivot pin 35 cooperates with fastener 37 to mount anvil jaw 30 to staple carrying jaw 40 for pivotal movement thereof upon actuation of handle 20.

Figure 2:
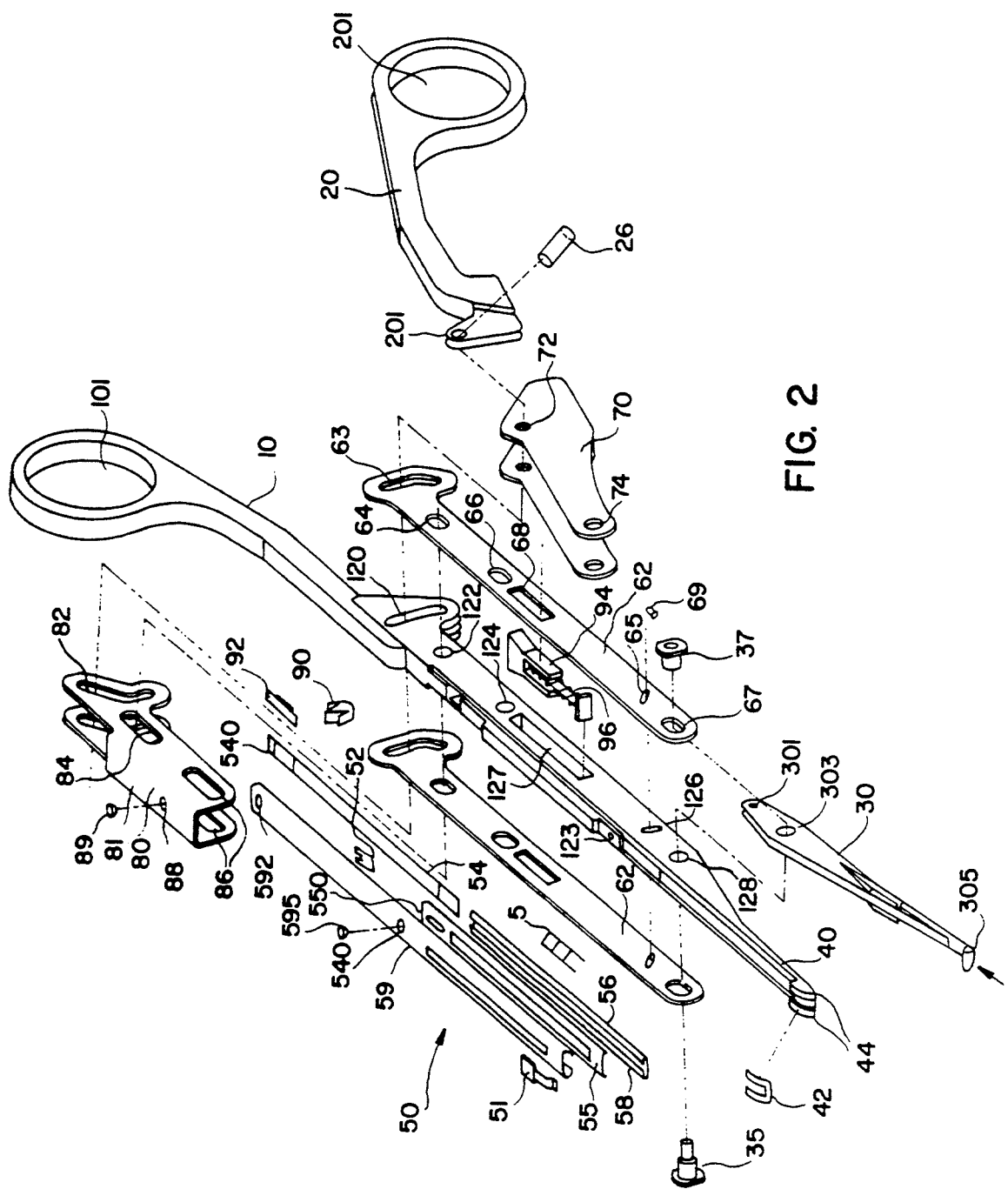
FIG. 2 is an exploded view showing the components of the apparatus of FIG. 1.

The linkage mechanism, as shown in the exploded view of FIG. 2, comprises a pair of elongated links 62, a mounting plate 70, and a saddle 80, all of which are mounted through aperture 201 of handle 20 and linkage track 120 of elongated handle 10 via guide pin 26. More specifically, guide pin 26 extends through mounting openings 72 in mounting plate 70 and slides in angled cam slots 63 of elongated links 62 and in angled tracks 82 of saddle 80. Pivot pin 35 extends through slots 67 in elongated links 62, holes 303 in anvil jaw 30, and aperture 128 in elongated handle 10. A camming pin 69 is mounted through rear opening 301 in anvil jaw 30, diagonal slots 65 in elongated links 62 and small slot 126 in elongated handle 10. When handle 20 is initially pivoted towards elongated handle 10, guide pin 26 travels upwardly in the vertical portion of angled track 82 and diagonally in the slanted portion of angled cam slot 63. As a result of this first movement of handle 20, saddle 80 remains stationary while mounting plate 70 pivots to drive elongated links 62 distally causing anvil jaw 30 to pivot around pivot pin 35 as camming pin 69 slides diagonally rearwardly in diagonal slots 65. This clamping position of the jaws is shown in FIG. 3.

Further mounting of the components of the linkage mechanism is apparent from FIG. 2 wherein mounting slots 64 of elongated links 62 are in alignment with hole 122 of elongated handle 10, elongated slots 66 are in alignment with hole 124, and central channels 68 are in alignment with central elongated channel 127. Saddle 80 straddles elongated links 62, so that central longitudinal channels 84 cooperate with mounting slots 64 and distal longitudinal channels 86 cooperate with elongated slots 66. Mounting plate 70 straddles saddle 80 such that its distal apertures 74 are aligned with distal longitudinal channels 86. Note that only one of the links 62 is labelled in FIG. 2 for purposes of clarity.

A handle return mechanism is provided which includes a bracket 94 and a coil spring 96. Bracket 94 is mounted within channel 127 of elongated handle 10 and central channels 68 of elongated links 62, and biases elongated links 62 in a proximal rest position.

Turning now to the staple jaw 40 and staple cartridge, a pair of curved staple surfaces 44 to support and guide the staple into contact with the anvil depressions are provided. Retaining plate 42 is secured atop curved staple surfaces 44 and retains and bends the staple pusher around these surfaces in the manner described below.

The staple cartridge, designated generally by reference numeral 50, and with reference to FIGS. 2, 6A and 7A, includes a fixed lower rack 54 mounted within a retaining channel 56, an upper rack 55 mounted over retaining channel 56, and a cartridge cover 59. A plurality of staples are aligned longitudinally in channel 56, with the legs pointing distally so that the legs of each staple contacts the crown portion of the next staple. Rails 58 of retaining channel 56 prevent transverse movement of the staples with respect to the longitudinal axis. Pusher finger 51 is welded to an upper surface portion of cartridge cover 59 and is configured to contact the crown of the distalmost staple to advance it towards anvil jaw 30. Pusher finger 51 slides underneath retaining plate 42 of jaw 40, and is flexed by the retaining plate 42 around curved surfaces 44. A stack pusher 52 is mounted between lower and upper racks 54, 55 and positioned behind the proximalmost staple of the stack of staples to push the entire stack distally so that the distalmost staple is positioned proximal to curved surfaces 44 of staple jaw 40 for engagement and subsequent advancement by pusher finger 51.

Figure 8B:
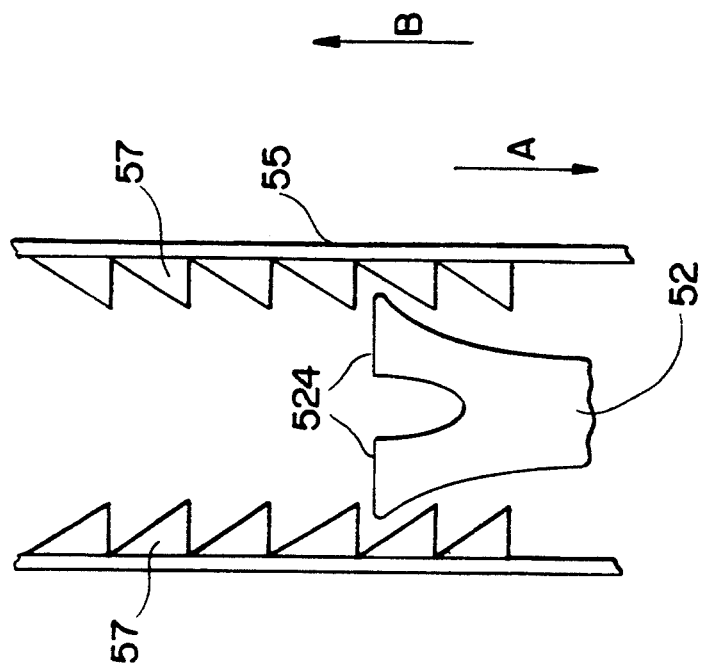
FIG. 8B is an enlarged bottom view showing the engagement of the stack pusher with the teeth of the upper rack.
Figure 8A:
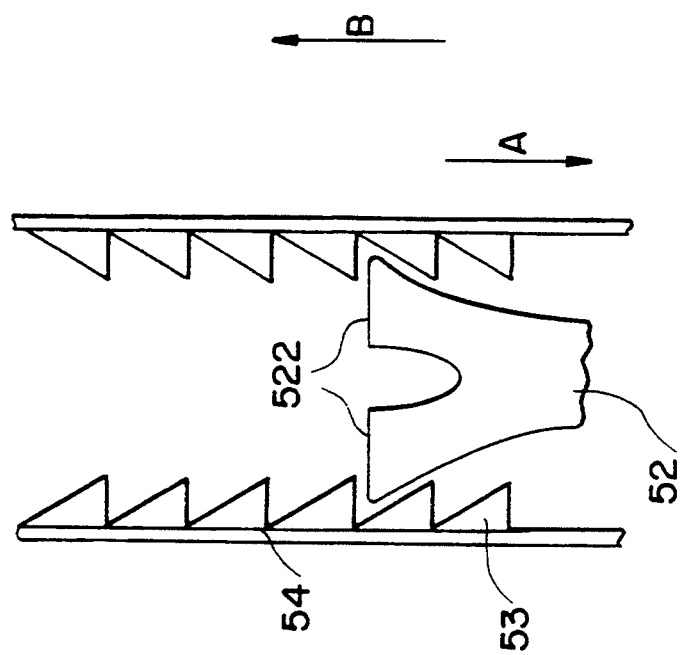
FIG. 8A is an enlarged top view showing the stack pusher in engagement with the teeth of the lower rack.

Lower rack 54, fixedly mounted atop handle 10 through aligned rear opening 540 and hole 123, includes a set of bottom teeth 53 (see also FIG. 8A) longitudinally aligned along each of its sides to receive a pair of bottom wings 522 of stack pusher 52. Top wings 524 of stack pusher 52 engage the upper teeth 57 (FIG. 8B) which are also formed on both sides of upper rack 55. Bottom teeth 53 and upper teeth 57 are configured and angled as shown to advantageously allow stack pusher 52 to move distally in the direction of arrow A when upper rack 55 is advanced while preventing proximal movement in the direction of arrow B when upper rack 55 is retracted as described below.

Cartridge cover 59 in conjunction with sliding movement of saddle 80 provides a mechanism for driving pusher finger 51 to advance each individual staple into the tissue as well as a mechanism for driving stack pusher 52 to advance the entire stack of staples. Cartridge cover 59 is mounted to saddle 80 by fastener 89 extending through aligned top opening 88 and rear hole 592. Cartridge pin 595 extends through hole 590 in cover 59 into slidable engagement with slot 550 in upper rack 55. When saddle 80 is biased distally upon continued actuation of handle 20 as described below, cartridge cover 59 slides forwardly with pin 595 sliding in slot 550. Thus, stack pusher 52 remains seated in upper and bottom teeth 57, 53 and pusher finger 51 is advanced into contact with the distalmost staple. When cartridge pin 595 reaches the distal edge of slot 550 as shown in phantom in FIG. 7B, upper rack 55 is engaged and is carried forwardly by pin 595. This advances stack pusher 52 in the direction of arrow A of FIGS. 8A and 8B a sufficient distance to advance the distalmost staple into position for engagement by distal finger 52 on the next firing stroke. Incremental movement of stack pusher 52 is ensured by teeth 57, 53.

Figure 5A:
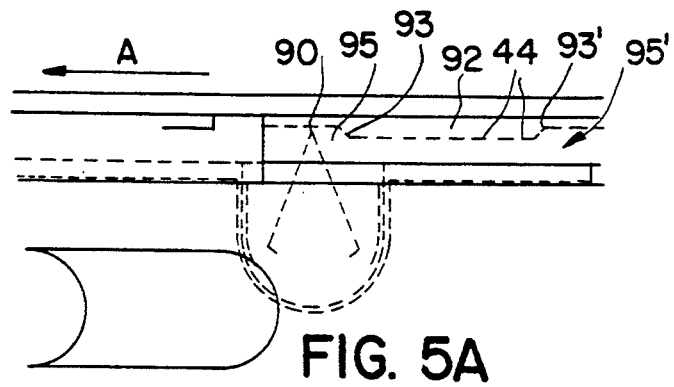
FIG. 5A is a side view of the ratchet mechanism of the present invention prior to initiation of the firing stroke.
Figure 5B:
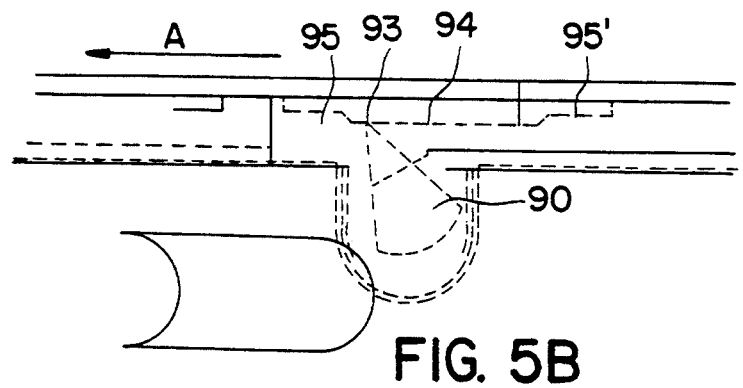
FIG. 5B is a side view showing the ratchet mechanism during firing.
Figure 5C:
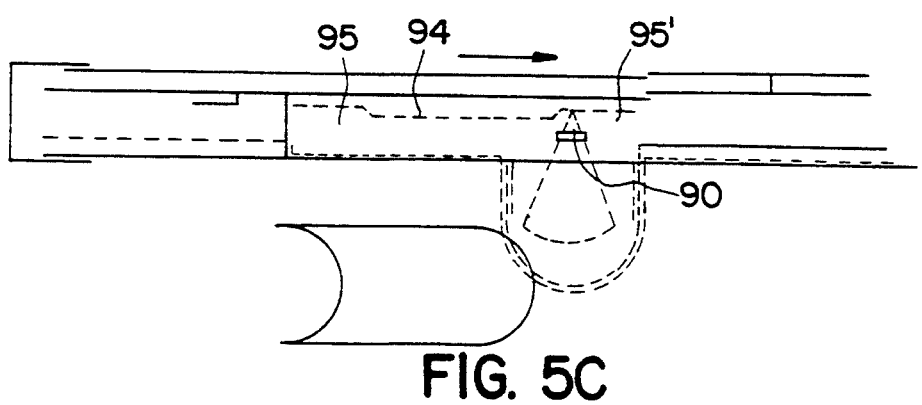
FIG. 5C is a side view showing the ratchet mechanism after completion of the firing stroke.
Figure 5D:
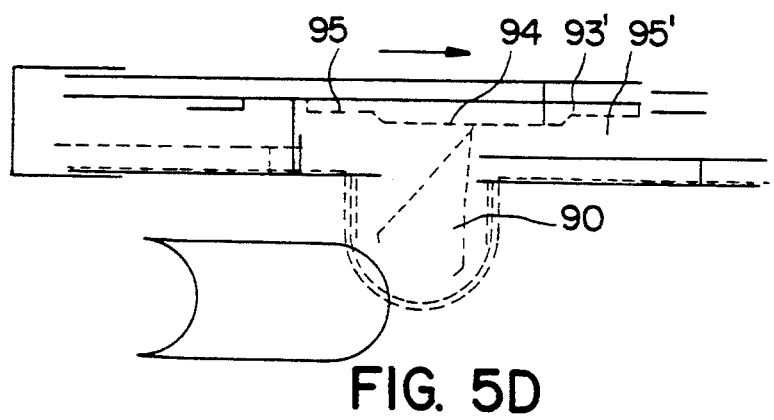
FIG. 5D is a side view of the ratchet mechanism during the return stroke.

A ratchet mechanism comprising a ratchet 90 and ratchet plate 92 is provided as a safety mechanism to require completion of a staple firing stroke once initiated. Ratchet plate 92 is attached to the inner surface of the upper wall 81 of saddle 80 by welding or any other suitable means. Ratchet 90 sits within a recess in elongated handle 10, with its tooth portion extending upwardly into contact with ratchet plate 92, as best shown in FIG. 1 and in the enlarged view of FIG. 5A. Ratchet plate 92 includes recessed portions 95, 95' at each end, central planar surface 94, and camming surfaces 93, 93'. When ratchet plate 92 is carried forwardly by saddle 80 in the direction of arrow A of FIGS. 5A and 5B, the tooth portion of ratchet 90 rides along camming surface 93 and is biased distally by planar surface 92. In this forwardly biased position, ratchet 90 effectively prevents ratchet plate 92 from sliding rearwardly until rear recess 95' is positioned thereabove and the tooth portion is allowed to pivot back to its vertical position as shown in FIG. 5C. At this point the staple firing stroke is completed. The return of ratchet plate 92 to its retracted position biases ratchet 90 rearwardly (FIG. 5D) as it rides over camming surface 93' and into engagement with planar surface 94. Ratchet 90 returns to its vertical position when ratchet plate 92 is retracted sufficiently rearwardly such that recessed portion 95 overlies the tooth portion as shown in FIG. 5A.

Turning now to the operation of the instrument, in the open position as shown in FIG. 1, handles 10 and 20 are spaced apart so that anvil jaw 30 is spaced from staple jaw 40. In this position, guide pin 26 is seated in the lowermost position of angled cam slots 63 of elongated links 62 and in the lowermost position of angled track 82 of saddle 80. It is also positioned at the bottom of linkage track 120 of elongated handle 10. Further, as shown in this Figure, mounting plate connecting pin 107, which extends through distal aperture 74 of mounting plate 70, is located in the distalmost position of longitudinal slots 66 of elongated links 62 and is seated through hole 124 of elongated handle 10. Proximal connecting pin 103 is positioned in the distalmost portion of aligned mounting slots 64 of elongated links 62 and in hole 122 of elongated handle 10. In this open position, cam pin 69 is located in the uppermost region at the intersection of diagonal slot 65 of elongated link 62 and small slot 126 of elongated handle 10.

Upon initial squeezing of actuating handle 20 towards stationary elongated handle 20, guide pin 26 travels diagonally upwardly in angled cam slot 63, thereby causing elongated link 62 to move proximally. As a result of this first movement of actuating handle 20, anvil jaw 30 pivots upwardly around pivot pin 35 to the closed position of FIG. 3 as pin 69 travels obliquely downwardly in diagonal slot 65. Thus, tissue is effectively clamped between anvil jaw 30 and staple jaw 40.

Note that in this clamped position, actuation of the staple firing mechanism has not yet been initiated so that advantageously the surgeon can reopen the handles 10, 20 and re-clamp the tissue at the same location or at an alternative surgical site.

Once the jaws are in the clamped position, and the handles are continuously squeezed, the absence of movement of anvil jaw 30 is felt by the user, thereby indicating the completion of the clamping cycle and warning that the staple advancing cycle is about to begin. Thus, in this second movement of handle 20 the jaws remain stationary and the staple pusher mechanism is not actuated. This "dwell position" corresponds to the point when guide pin 26 has completed its diagonally directed travel in angled cam slot 63 but has not yet started its oblique travel in angled track 82, i.e. is in the overlapping vertical portions of slot 63 and track 82. In this dwell position, the handles 10, 20 and jaws 30, 40 can advantageously be opened to allow re-clamping of the tissue. Therefore, this dwell position advantageously signals the user that the staple advancing mechanism will be actuated if the handles are continued to be squeezed, but provides sufficient time to unclamp the tissue prior to such actuation.

Figure 4:
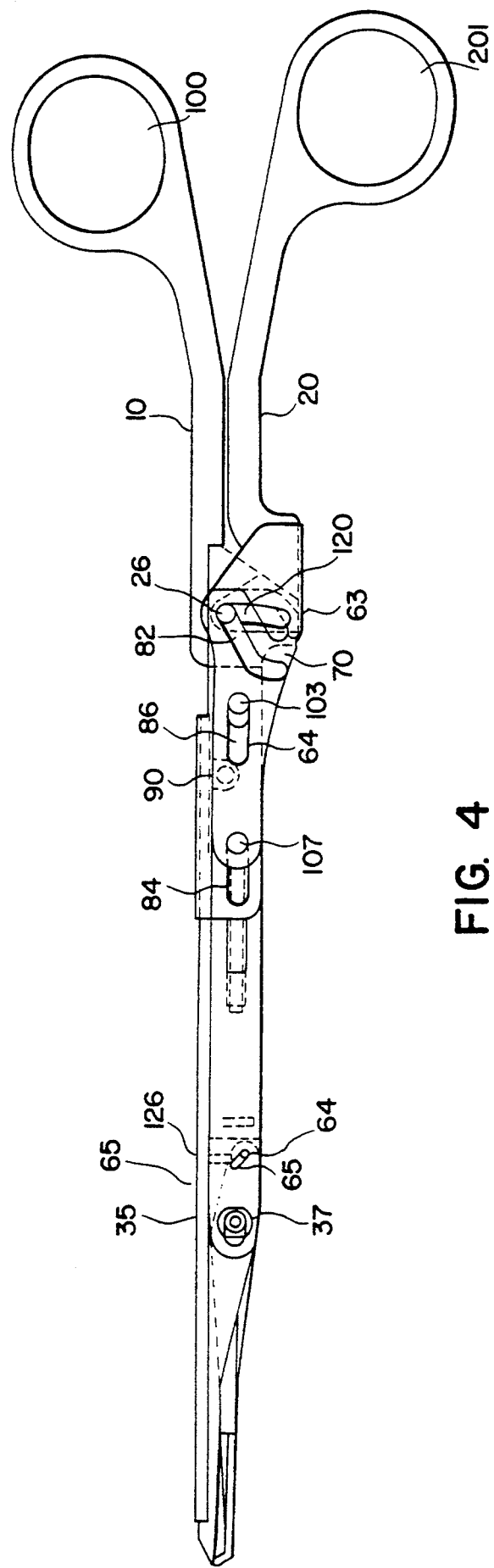
FIG. 4 is a side view showing the apparatus in the clamped and fired position.

If staple firing is desired, actuating handle 10 is continuously squeezed, causing guide pin 26 to travel diagonally upwardly in angled track 82 of saddle 80. This third movement of actuating handle 20 translates to distal movement of saddle 80 with longitudinal channels 84 and 86 travelling along fixed center connecting pin 107 and proximal connecting pin 103 as shown in FIG. 4. As saddle 80 is slid forwardly, camming surface 93 of ratchet 90 engages central planar surface 94 of ratchet plate 92, as shown in FIG. 5B to prevent proximal movement of saddle 80 until completion of the firing stroke.

Figure 6C:
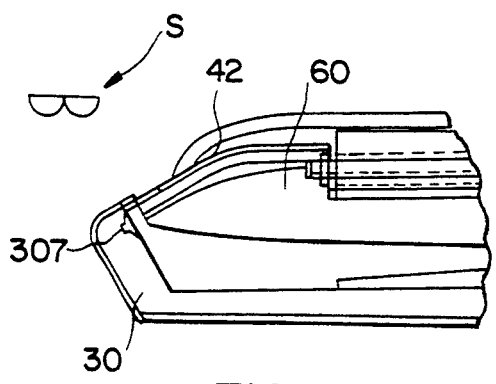
FIG. 6C is an enlarged side view of the distal end of the staple jaw and anvil jaw in the clamped, fired position.

Distal movement of saddle 80 slides channel cover 59 forwardly so that pusher finger 51, already in contact with the crown portion of the distalmost staple, (FIG. 6B) begins to advance the staple around curved surfaces 44. As channel cover 59 slides forwardly, upper rack 55, which up to this point had remained stationary, is engaged and carried forwardly as pin 595 abuts the distal edge of slot 550 (shown in phantom in FIG. 7B). Consequently, concurrent with the advancement of the staple over the curved surfaces 44 (FIG. 6C) and through the clamped tissue into contact with the anvil depressions 307, upper rack 55 is carried forwardly. Upper rack 55 moves stack pusher 52 distally a distance equal to the length of a staple, as its upper wings 524 and lower wings 522 step over upper teeth 57 and lower teeth 52, respectively. As a result, the stack of staples is advanced so the distalmost staple is moved to the ready position proximal to curved surfaces 44 for engagement by pusher finger 51 in the next firing stroke. The positioning of the components upon firing of the apparatus is shown in FIG. 4, with guide pin 26 in the uppermost region of angled track 82 and pins 107, 103 in the proximalmost portion of channels 84, 86.

In the return stroke after firing of the staple, handle 20 is released and guide pin 26 travels diagonally forwardly in angled track 82 of saddle 80 to retract saddle 80 proximally. Proximal movement of saddle 80 retracts cover 59 and subsequently upper rack 55 as pin 595 engages the proximal edge of slot 550. The engagement of lower wings 522 with lower teeth 53 of lower rack 54 prevents stack pusher 52 from being retracted along with upper rack 55. Pusher finger 51 steps over the distalmost staple and returns to its retracted position in contact with the crown portion of the distalmost staple.

The biasing force of return spring 96 on elongated links 62 causes guide pin 26 to travel obliquely in angled cam slot 63, thereby causing retraction of elongated links 62 concommitant with opening of the handles 10,20. The instrument is thus returned to the initial position of FIG. 1.

The instrument of the present invention has particular application to vascular tissue, although it can be used to attach or close openings in other types of body tissue. The clamping and closing of individual vessels to effect hemostasis by the stapling apparatus of the present invention saves the surgeon valuable time. The stapling apparatus of the present invention can also be used to attach approximated vessels or vessel portions by inserting each leg of the staple through one of the approximated vessels or vessel portions. The B-shaped formation of the legs provides advantageous attachment of the approximated vessels.

The instrument of the present invention can also be used in laparoscopic or endoscopic procedures. That is, the instrument with its handles and jaws closed, can be inserted through a small incision in the body or through a narrow endoscopic tube which is positioned through a small opening in the skin and extends into the interior of the body. After insertion, the jaws can be opened and then closed around the body tissue, and a staple can be applied by further manipulation of the handles.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical stapling apparatus comprising:
    first and second handles;
    an anvil jaw pivotally connected to said first handle for movement from an open position to a closed position to clamp body tissue;
    staple advancing means for advancing an individual staple into contact with said anvil jaw for deformation of the staple legs;
    means responsive to movement of said first handle for closing the anvil jaw and for driving the staple advancing means in a three phase movement of said first handle wherein in a first movement of said first handle said anvil jaw pivots to a closed position, in a second subsequent movement of said first handle comprising a dwell period in which said anvil jaw remains stationary and said staple advancing means is not yet actuated, and in a third movement of said first handle said staple advancing means is driven to advance a staple through the tissue and into contact with said anvil jaw; and
    means for tactilely indicating to a user the termination of said first movement, said indicating means including means for providing said dwell period comprising said second subsequent movement of said first handle.

2. An apparatus as recited in claim 1, wherein said means for closing said anvil jaw and for driving said advancing means includes cam means positioned between said first handle and said staple advancing means, said cam means configured to open and close said anvil jaw and to drive said advancing means in response to movement of said first handle.

3. An apparatus as recited in claim 2, wherein said cam means for closing said anvil jaw comprises a camming slot having an angled portion and a vertical portion.

4. An apparatus as recited in claim 3, wherein said cam means for driving said staple advancing means comprises a camming slot having a vertical portion and an angled portion.

5. An apparatus as recited in claim 4, wherein said angled portion of said camming slot for closing said anvil jaw terminates below said angled portion of said camming slot for said staple advancing means so at least a portion of said vertical portions of said camming slots overlap.

6. An apparatus as recited in claim 2 wherein said cam meads comprises a first link member connecting said first handle to said anvil jaw, said first link member including a camming slot cooperating with a pin connected to said first handle.

7. An apparatus as recited in claim 6, wherein said camming slot has an angled portion and a vertical portion, wherein said pin first travels in said angled portion to advance said first link member to pivot said anvil jaw to a closed position, and when said pin subsequently travels in said vertical portion, said first link member remains stationary.

8. An apparatus as recited in claim 7, further comprising a second link member connecting said second handle to said staple advancing means, said second link member including a camming slot cooperating with a pin connected to said second handle.

9. An apparatus as recited in claim 8, wherein said camming slot of said second link member has a vertical portion and an angled portion, wherein when said pin connected to said second handle first travels in said vertical portion of said second link, said second link member remains stationary, and when said pin connected to said second handle subsequently travels in said angled portion of said second link, said second link member is advanced distally.

10. An apparatus as recited in claim 9, wherein said vertical portions of both said camming slots overlap, and said second movement of said first handle causes said pin to travel in said overlapping vertical portions.

11. An apparatus as recited in claim 10, wherein said anvil jaw has a slot cooperating with a slot in said first link member.

12. An apparatus as recited in claim 6, further including spring means coupled to said first link member to bias said first link member to a distal position such that said anvil jaw is biased to an open position.

13. An apparatus as recited in claim 6, wherein said first link member includes a second slot cooperating with a slot formed in said anvil jaw to receive a camming pin, said camming pin pivoting said anvil jaw to said closed position upon first movement of said first handle.

14. An apparatus as recited in claim 13, wherein said first link member is adapted to advance proximally during said first movement of said first handle.

15. An apparatus as recited in claim 2, wherein said cam comprises a link member connecting said second handle to said staple advancing means, said link member including a camming slot cooperating with a pin connected to said second handle.

16. An apparatus as recited in claim 15, wherein said camming slot of said second link member has a vertical portion and an angled portion, wherein when said pin first travels in said vertical portion said link member remains stationary, and when said pin subsequently travels in said angled portion said link member is advanced distally.

17. An apparatus as recited in claim 16, wherein said second link member is advanced distally during said third movement of said first handle.

18. An apparatus as recited in claim 1, further comprising a staple cartridge containing a stack of staples, and means for advancing said stack of staples, said staple stack advancing means comprises a first toothed rack engaging a staple stack pusher, said rack movable during said third movement of said first handle.

19. An apparatus as recited in claim 18, further comprising a second toothed rack positioned opposite said first toothed rack and engaging said stack pusher.

20. An apparatus as recited in claim 19, wherein said second toothed rack remains stationary during movement of said first toothed rack.

21. An apparatus as recited in claim 20 wherein said means for actuating said staple advancing means comprises link means for connecting said staple advancing means to said first handle, 22. An apparatus as recited in claim 21, wherein said link means includes a camming slot cooperating with a guide pin connected to said first handle.

23. An apparatus as recited in claim 22, wherein said staple advancing means includes a staple pusher for engagement with a distalmost staple.

24. An apparatus as recited in claim 1, further comprising a ratchet mechanism for preventing retraction of said staple advancing means until completion of a firing stroke.

25. An apparatus as recited in claim 24, wherein said ratchet mechanism includes a toothed member engageable with a plate.

26. A surgical stapling apparatus comprising:
a first handle;
a staple cartridge communicating with said first handle, said staple cartridge containing a plurality of staples aligned in a row;
a second handle pivotally mounted to said first handle;
an anvil jaw linked to said second handle and movable in response to a first movement of said second handle to clamp tissue;
means responsive to a subsequent movement of said second handle for advancing a staple into Contact with said at least one staple forming depression of said anvil jaw to deform the legs of the staple; and
means for tactilely indicating to a user the termination of said first movement, said indicating means comprising means for providing a dwell position of said staple advancing means between said first and subsequent movements in which said second handle is pivoted and said anvil jaw is not pivoted and said staple advancing means is not actuated.

27. An apparatus as recited in claim 26 wherein said first handle further comprises a curved staple guiding surface to orient the staple prior to contact with said anvil jaw.

28. A surgical staple cartridge comprising:
a first rack having a plurality of teeth;
a stack of staples longitudinally aligned in said first rack;
means for advancing said staple stack distally said advancing means comprising a stack pusher positioned proximal to and abutting a proximalmost staple and engaging said teeth of said first rack; and
means for advancing said stack pusher distally, said advancing means including means engaging said teeth of said first rack for preventing proximal movement of said stack pusher.

29. A staple cartridge as recited in claim 28, wherein said stack pusher advancing means comprises a second rack positioned over said first rack and said preventing means comprises a plurality of teeth formed in said second rack and engaging said stack pusher.

30. A cartridge as recited in claim 29, further comprising staple pusher means for advancing a distalmost staple into body tissue, said staple pusher means engaging said second rack to carry it distally to advance said stack pusher only after said staple advancing means has moved a predetermined distance.

31. A cartridge as recited in claim 30, wherein said staple advancing means includes a staple pusher finger for advancing an individual staple.

32. A surgical staple cartridge comprising:
a plurality of staples aligned in a longitudinal row;
a slidable rack having a plurality of teeth formed therein;
a stack pusher engaged within said plurality of teeth of said slidable rack and mounted proximal to anti abutting a proximalmost staple;
means for sliding said slidable rack distally to drive said stack pusher to advance a staple, said sliding means including means engaging with said teeth for preventing proximal movement of said stack pusher.

33. A surgical stapling apparatus comprising:
a staple cartridge containing a plurality of staples aligned in a row;
an anvil jaw having at least one staple forming depression formed thereon disposed opposite said staple cartridge and pivotably mounted for movement between open and closed positions;
a staple pusher for advancing a distal most staple into contact with said anvil jaw;
a stack pusher positioned at a proximal end of said row of staples for advancing the entire row of staples;
means for driving said staple pusher and said stack pusher to advance said staple pusher and to advance said row of staples during a dwell period following partial advancement of said staple pusher but prior to full advancement of said staple pusher; and
means for tactilely indicating to a user the termination of said partial advancement of said staple pusher, said indicating means including means for providing said dwell period comprising a time during which said anvil jaw and said staple cartridge move between a position in which said anvil jaw is in said closed position and said staple pusher is in a partially advanced position.

34. An apparatus as recited in claim 33, further comprising a handle linked to said actuating means, wherein pivotal movement of said handle advances said actuating means.

35. An apparatus as recited in claim 34, wherein said handle is further linked to said anvil jaw such that pivotal movement of said handle pivots said anvil jaw.

* * * * *